United States Patent [19]

Casado et al.

[11] Patent Number: 5,684,206
[45] Date of Patent: Nov. 4, 1997

[54] β-AMINOVINYL KETONES, A PREPARATION PROCESS AND THEIR USE IN THE PREPARATION OF β-DIKETONES

[75] Inventors: Michel Casado, St. Symphorien D'Ozon; Pierre Le Roy; Virginie Pevere, both of Lyons, all of France

[73] Assignee: Rhone-Poulenc Argochimie, Lyons Cedex, France

[21] Appl. No.: 569,266
[22] PCT Filed: Jun. 16, 1994
[86] PCT No.: PCT/FR94/00726
§ 371 Date: Mar. 20, 1996
§ 102(e) Date: Mar. 20, 1996
[87] PCT Pub. No.: WO95/00476
PCT Pub. Date: Jan. 5, 1995

[30] Foreign Application Priority Data

Jun. 23, 1993 [FR] France .................. 93 07867

[51] Int. Cl.⁶ .................................... C07C 49/76
[52] U.S. Cl. .................. 568/336; 568/383; 549/355; 549/498; 549/499
[58] Field of Search ............... 568/383, 336; 549/355, 498, 499

[56] References Cited

FOREIGN PATENT DOCUMENTS

| 0487870 | 9/1991 | European Pat. Off. . |
| 0487870 | 6/1992 | European Pat. Off. . |

OTHER PUBLICATIONS

Journal of Organic Chemistry;USSR;26#10;pp. 1801–1805; 1990.
Journal of Organic Chemistry;USSR;22#4;pp. 790–791;Sosnovskikh et al, 1986.
Journal of Organic Chemistry; 53#11;pp. 2426–2429, 1988.
Journal of the Chemical Society;Perkin Trans.1;#7; pp. 1401–1406;Nitta et al, 1985.
LA Chimica EL'Industria;vol. 56 #1;pp. 25–26;P.Barvo et al, 1974.
Sosnovskikh et al, *Journal of Organic Chemistry of the USSR*, vol. 26, No. 10, pp. 1801–1805, Oct. 1990.
Sosnovskikh et al, *Journal of Organic Chemistry of the USSR*, vol. 22, No. 4, pp. 790–791, Apr. 1986.
Guarna et al, *Journal of Organic Chemistry*, vol. 53, No. 11, pp. 2426–2429, May 1988.

*Primary Examiner*—C. Warren Ivy
*Assistant Examiner*—Sreeni Padmanabhan
*Attorney, Agent, or Firm*—Burns, Doane, Swecker & Mathis, L.L.P.

[57] ABSTRACT

Novel β-aminovinyl ketones of the general formula

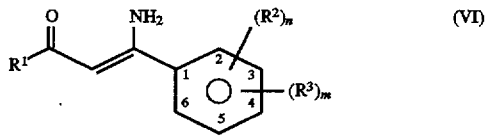

(VI)

wherein $R^1$ is, in particular, an alkenyl, alkynyl, cycloalkyl or cycloalkenyl group; $R^2$ is, in particular, an electron-attracting substituent such as nitro, acyl, ester, alkylthio, carbamoyl, thiocarbamoyl or haloalkyl; $R^3$ is, in particular, an alkyl or alkoxy group or a halogen atom; n is 1 or 2 and m is 0, 1, 2 or 3. A method for preparing such compounds by carrying out a condensation reaction between ketone $R^1$—CO—$CH_3$ and, in particular, benzonitrile substituted by $(R^2)_n$ and optionally $(R^3)_m$, in the presence of a strong base, as well as a process employing said β-aminovinyl ketones of general formula (VI) for preparing the corresponding β-diketones, are also disclosed.

18 Claims, No Drawings

β-AMINOVINYL KETONES, A PREPARATION PROCESS AND THEIR USE IN THE PREPARATION OF β-DIKETONES

This Application is the US National stage of PCT/FR94/00726 filed Jun. 16, 1994 which was published on Jan. 5, 1995 as WO95/00476.

The present invention relates to new β-aminovinyl ketones having an aromatic substituent on the carbon attached to the amino group, to a process for the preparation of these compounds from nitriles and from a methyl organo ketone and to their use in the preparation of aromatic β-diketones.

TECHNICAL CONTEXT OF THE INVENTION

Aromatic β-diketones of general formula:

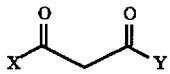   (I)

in which the X symbol represents, for example, an aliphatic or cycloaliphatic group and Y represents, for example, an aromatic group, can advantageously be used as intermediates in the synthesis of 4-benzoylisoxazole derivatives of general formula:

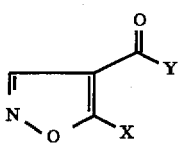   (II)

which can be broad-spectrum herbicides which are well known in the prior state of the art (cf. in particular EP-A-0,418,175).

The synthesis of a 4-benzoylisoxazole derivative from a diketone of formula (I) can be carried out by linking together the following two stages:

reaction of the diketone of formula (I) with a trialkyl orthoformate or a dimethylformamide dialkyl acetal to lead to a product corresponding to the general formula:

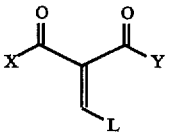   (III)

in which L is an O-alkyl group or an N,N-dialkylamino group; this reaction is generally carried out in an inert solvent such as, for example, diethyl ether or tetrahydrofuran, at a temperature ranging from 0° C. to the reflux temperature of the mixture; and reaction of the compound of formula (III) with a hydroxylamine salt; this reaction is generally carried out in a solvent such as, for example, ethanol or acetonitrile, optionally in the presence of a base or of an acid acceptor such as, for example, triethylamine or sodium acetate.

As regards the starting β-diketone of formula (I), its synthesis is commonly carried out by linking together the following three stages:

hydrolysis reaction of an aromatic nitrile of general formula:

Y—CN   (IV)

to get the corresponding carboxylic acid;
preparation of an ester of this acid which is derived from an aliphatic alcohol such as, for example, methanol; and condensation reaction of the said ester with a ketone of general formula:

   (V)

this reaction being carried out in the presence of a strong base under conditions in accordance with the Claisen condensation.

PURPOSE OF THE PRESENT INVENTION

The essential purpose of the present invention is that of proposing:

an access route starting from an aromatic nitrile and leading to β-diketones which are capable of being used as intermediates in the synthesis of 4-benzoylisoxazole derivatives, which has many advantages: the number of stages is limited, the yields are excellent and the process is genuinely easy to develop on an industrial scale.

According to this access route, a β-aminovinyl ketone which has an aromatic substituent on the carbon attached to the amino group is prepared which has the double characteristic of being a compound which, on the one hand, is novel and which, on the other hand, can be easily converted to the desired β-diketone by subjecting, to the conversion reaction, either the aminovinyl ketone isolated from the reaction mixture in which it has been prepared or directly the said reaction mixture containing the aminovinyl ketone.

DESCRIPTION OF THE PRESENT INVENTION

I—In its first subject, the present invention relates to a β-aminovinyl ketone of general formula:

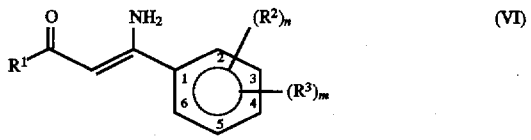   (VI)

in which:

$R^1$ represents:

a straight- or branched-chain alkenyl or alkynyl group containing up to 6 carbon atoms which is optionally substituted with one or a number of halogen atom(s) and whose unsaturation is not conjugated with the ketone double bond;

a cycloalkyl group containing 3 to 6 carbon atoms, optionally substituted with one or a number of $R^4$ or $OR^4$ group(s) or one or a number of halogen atom(s);

a cycloalkenyl group containing 4 to 6 carbon atoms, optionally substituted with one or a number of $R^4$ or $OR^4$ group(s) or one or a number of halogen atom(s), in which the ethylenic unsaturation is not conjugated with the ketone double bond;

a group of formula $(R^5\!\!-\!\!)_p\text{phenyl-}(CR^6R^7)_q\text{—}$;

$R^4$ being a straight- or branched-chain alkyl group containing up to 4 carbon atoms;

$R^5$ being a straight- or branched-chain alkyl group containing up to 4 carbon atoms or a halogen atom (F, Cl, Br or I);

$R^6$ and $R^7$, which can be identical or different, each representing a straight- or branched-chain alkyl group containing up to 4 carbon atoms;

p and q being integers, which can be identical or different, ranging from 0 to 3;

$R^2$ represents an electron-withdrawing substituent chosen from the group formed by:
- a nitro group;
- a $COR^4$ acyl group;
- a $COOR^8$ group;
- an $SR^4$ alkylthio group;
- a $CONR^8R^9$ carbamoyl or $CSNR^8R^9$ thiocarbamoyl group;
- a linear or branched haloalkyl or haloalkoxy group having up to 4 carbon atoms and in which the halo substitution is a monosubstitution which can range up to a virtually complete polysubstitution;
- $R^4$ having the general definitions shown above;
- $R^8$ and $R^9$, which can be identical or different, each representing a hydrogen atom or a straight- or branched-chain alkyl group containing up to 4 carbon atoms;

$R^3$ represents:
- a straight- or branched-chain alkyl or alkoxy group containing up to 4 carbon atoms, it being possible for the alkyl group to be optionally substituted with an $OR^4$ group;
- a halogen atom;
- a group of formula $O$-$(CH_2)_r$-$OR^4$;
- $R^4$ possessing the general definition shown above and r being an integer ranging from 1 to 4;

the n symbol represents an integer ranging from 0 to 2 and the m symbol represents an integer ranging from 0 to 3;
with the following provisos a) and b):
a) $R^5$ is other than a chlorine atom when $R^3$ is a chlorine atom and q=0,
b) when n, m and q are all equal to zero, then p is other than zero.

Mention may be made, as β-aminovinyl ketones preferentially representative of the present invention taken from its first subject, of those which correspond to the formula (VI) in which the n symbol represents a number ranging from 1 to 2 and the m symbol represents a number ranging from 0 to 3.

Mention may be made, as more preferentially representative β-aminovinyl ketones, of the compounds of formula (VI), belonging to the preferentially representative group targeted in the preceding paragraph, in the structure of which:
$R^1$ represents a cycloalkyl group containing 3 to 6 carbon atoms, optionally substituted with one or a number of $R^4$ or $OR^4$ group(s);
$R^2$ represents an $SR^4$ alkylthio group or a linear or branched haloalkyl or haloalkoxy group having up to 4 carbon atoms and in which the halo substitution is a monosubstitution which can range up to a virtually complete polysubstitution;
$R^3$ represents a straight- or branched-chain alkyl or alkoxy group containing up to 4 carbon atoms or a halogen atom.

Mention may be made, as still more preferentially representative β-aminovinyl ketones, of the compounds, belonging to the more preferentially representative group targeted in the preceding paragraph, in the structure of which:
the n symbol represents an integer equal to 1 or 2 and the m symbol represents an integer ranging from 0 to 2, with the additional condition according to which the sum of m+n is not more than 3;
the group or one of the groups represented by $(R^2)_n$ is in the 2-position on the phenyl ring whereas the optional other group(s) represented by $(R^2)_n$ and/or $(R^3)_m$ are in the 3- and/or 4-position on the phenyl ring.

Mention may be made, as very particularly representative β-aminovinyl ketones, of the compounds of formula (VI), belonging to the still more preferentially representative group targeted in the preceding paragraph, in the structure of which:
$R^1$ represents a cyclopropyl or 1-methylcyclopropyl group;
$R^2$ represents a methylthio or ethylthio group or a trifluoromethyl or trifluoromethoxy group;
$R^3$ represents a methyl, ethyl, methoxy or ethoxy group or a chlorine, bromine or fluorine atom.

Mention will especially be made, as specific examples of β-aminovinyl ketones, of the following compounds:
1. 1-amino-3-cyclopropyl-1-(2-methylthio-4-chlorophenyl)-1-propen-3-one;
2. 1-amino-3-cyclopropyl-1-(2-methylthio-4-trifluoromethylphenyl)-1-propen-3-one;
3. 1-amino-3-cyclopropyl-1-(2-methylthio-4-bromophenyl)-1-propen-3-one;
4. 1-amino-3-cyclopropyl-1-(2-methylthio-3,4-dichlorophenyl)-1-propen-3-one;
5. 1-amino-3-cyclopropyl-1-(2-methyl-4-methylthiophenyl)-1-propen-3-one;
6. 1-amino-3-cyclopropyl-1-(2-methylthio-3-chloro-4-bromophenyl)-1-propen-3-one;
7. 1-amino-3-cyclopropyl-1-(2-methylthio-3-ethoxy-4-chlorophenyl)-1-propen-3-one;
8. 1-amino-3-cyclopropyl-1-(2-methylthio-3,4-dibromophenyl)-1-propen-3-one.

II—In its second subject, the present invention relates to a process for the preparation of β-aminovinyl ketones of formula (VI) or of mixtures based on aminovinyl ketones, which is characterized in that it comprises the condensation reaction of a methyl organo ketone of formula:

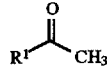
(VII)

in which $R^1$ has one of the general or preferred definitions shown above with respect to the formula (VI), with an aromatic nitrile of formula:

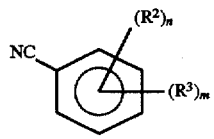
(VIII)

in which the $R^2$, $R^3$, n and m symbols have one of the general or preferred definitions shown above with respect to the formula (VI), the said condensation reaction being carried out under an inert atmosphere, with prolonged heating, in inert solvent medium, in the presence of a strong base taken from the group formed by:
(i) alkoxides derived from alkali metals and primary monoalcohols in the structure of which the residue associated with the $CH_2OH$ group is a branched-chain group in which the carbon atom directly bonded to the $CH_2OH$ group is itself bonded to 2 or 3 other carbon atoms, these other carbon atoms belonging to identical or different radicals each chosen from a linear or branched alkyl radical having up to 3 carbon atoms and a phenyl radical;
(2i) alkoxides derived from alkali metals and secondary or tertiary monoalcohols in the structure of which each of the 2 identical or different residues associated with the CHOH group, in the case of secondary alcohols, or each of the 3 identical or different residues associated with the COH group, in the case of tertiary alcohols, consists of a radical chosen from a linear or branched alkyl radical having up to 4 carbon atoms and a phenyl radical; and (3i) solutions of the (i) or (2i) alkoxides in the monoalcohols in which they have been prepared.

The condensation reaction is generally carried out under a slight positive pressure of an inert gas, such as, for example, nitrogen or argon, and in an inert solvent or a mixture of inert solvents.

Preferred solvents are water-immiscible aprotic polar solvents such as, for example, tetrahydrofuran, dioxane, diethyl ether, methyl tert-butyl ether, benzene, chlorobenzene or toluene.

The reaction is carried out at a temperature lying in the range from 30° C. to 120° C.; the temperature chosen is preferably that, in the abovementioned range, which corresponds to the reflux temperature of the reaction mixture.

The duration of the reaction can vary, depending on the temperature chosen, between, for example, 30 minutes and 5 hours.

The reaction is preferably carried out with the following molar proportions of ingredients:
aromatic nitrile of formula (VIII): 1 mol,
$R^1$ methyl ketone of formula (VII) : 1 to 4 mol and preferably 1.3 to 2 mol,
alkoxide : 1 to 4 mol and preferably 1.3 to 2 mol.

It is possible, as regards the strong base used, to resort, for example, to the sodium or potassium alkoxides derived from the following alcohols:

isobutyl alcohol $(CH_3)_2CH$—$CH_2OH$,
isopropyl alcohol $(CH_3)_2$—$CHOH$,
sec-butyl alcohol $CH_3(C_2H_5)$—$CHOH$,
tert-butyl alcohol $(CH_3)_3$—$COH$,
dimethylphenylmethyl alcohol $(CH_3)_2(C_6H_5)$—$COH$,
triphenylmethyl alcohol $(C_6H_5)_3$—$COH$, or to the solutions of these alkoxides in the abovementioned alcohols.

The best results are obtained by carrying out the condensation reaction in the presence of a strong base taken from the group formed by:

(4i) alkoxides derived from alkali metals and tertiary monoalcohols in the structure of which each of the 3 identical or different residues associated with the COH group is a radical chosen from a linear alkyl radical having 1 or 2 carbon atoms and a phenyl radical, such as, for example, the sodium and potassium alkoxides derived from the following alcohols of formula: $(CH_3)_3$—$COH$, $(CH_3)_2(C_6H_5)$—$COH$ and $(C_6H_5)_3$—$COH$; and (5i) solutions of the (4i) alkoxides in the monoalcohols in which they have been prepared.

The alkoxide can be prepared in various ways: the alkoxide can be prepared by dissolving the alkali metal in the corresponding alcohol; the alkoxide can alternatively be prepared by reacting an alkali metal methoxide with the corresponding alcohol; another way of carrying out the preparation consists alternatively in reacting an alkali metal hydride with the corresponding alcohol. The alkoxide can be prepared outside the medium of the condensation reaction or optionally in situ. This preparation is generally carried out, in a way known per se, by using 1 to 5 mol, and preferably 1.1 to 4 mol, of the corresponding alcohol per 1 mol of the alkaline reactant (alkali metal, alkali metal methoxide or alkali metal hydride). The alkoxide formed can be used either in the pure state or in the form of a solution in the unreacted alcohol in which it has been prepared, when the latter is used in excess. In the present specification, the term "solutions of the alkoxides in the monoalcohols in which they have been prepared" is understood to define solutions which can contain up to 4 mol of alcohol, and preferably between 0.1 and 3 mol of alcohol, per 1 mol of strong alkoxide base.

When all the nitrile of formula (VIII) has reacted, one way of ending the reaction can consist in cooling the reaction mixture, in bringing the pH to neutrality by addition of a predetermined amount of an inorganic oxyacid or hydracid and in adding a sufficient amount of water to dissolve the salts formed; the acid and the water can advantageously be introduced together in the form of a dilute aqueous solution of the acid.

When the condensation reaction is carried out in a water-immiscible solvent medium, an aqueous/organic two-phase mixture is obtained on conclusion of the treatment protocol which has just been described. The organic phase, which contains the aminovinyl ketone formed, is separated, for example by settling, and then concentrated by removal of the solvent(s).

The residual product thus obtained after removal of the solvent(s) consists essentially of the β-aminovinyl ketone of formula (VI). The expression "consists essentially" is intended to signify that the β-aminovinyl ketone can, in certain cases, be found in the residual product in the form of a mixture with a minor amount of by-product(s) consisting of:

a pyrimidine of general formula:

(IX)

and/or an amide of general formula:

(X)

in which formulae the Ar symbols, which are identical to each other and represent the group:

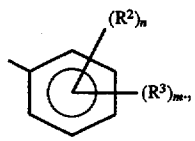

and the $R^1$ symbol have the general or preferred definitions shown above with respect to the aminovinyl ketone of formula (VI).

In the present specification, the expression "mixture based on aminovinyl ketone" will denote the residual product consisting of the mixture of β-aminovinyl ketone of formula (VI) with a minor amount of by-product(s) of formulae (IX) and/or (X). The amounts of by-product(s), expressed as mol % of by-product(s) in the mixture based on aminovinyl ketone, can be not more than:
pyrimidine of formula (IX): 14%,
amide of formula (X): 35%.

When the residual product is in the form of a mixture based on aminovinyl ketone, it is possible to obtain a β-aminovinyl ketone in the pure form by subjecting the mixture to a recrystallization operation in a suitable solvent such as, for example, toluene or toluene/cyclohexane mixtures.

When the condensation reaction is carried out in a water-miscible solvent medium, it is possible to isolate the β-aminovinyl ketone or a mixture based on aminovinyl ketone by subjecting the reaction mixture, after addition of acid and water, for example to an extraction operation with a suitable third solvent, optionally having removed all or part of the reaction solvent(s) beforehand.

III—In this third subject, the present invention relates to the use of the β-aminovinyl ketones of formula (VI) or of mixtures based on aminovinyl ketones in the preparation of β-diketones of general formula:

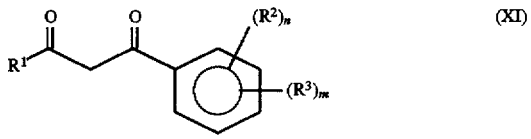
(XI)

in which the $R^1$, $R^2$, $R^3$, n and m symbols have one of the general or preferred definitions shown above with respect to the formula (VI), the said use being characterized in that it comprises the operation of subjecting a β-aminovinyl ketone of formula (VI) or a mixture based on aminovinyl ketone to a hydrolysis reaction, the hydrolysis reaction being carried out, optionally in an inert solvent medium, in the presence of water and a strong inorganic or organic acid.

The hydrolysis reaction can be carried out without solvent or in solvent medium by addition then to the starting reactants of an inert solvent or mixture of inert solvents.

When hydrolysis is carried out in solvent medium, which corresponds to a preferred procedure, use is advantageously made of a solvent medium which is identical to that used in the context of the process in accordance with the present invention taken from its second subject and in particular a solvent medium which is not only identical but is again polar, aprotic and water-immiscible. A still more preferred procedure then consists in using the β-aminovinyl ketone or the mixture based on aminovinyl ketone in the form of the organic phase as it is obtained, after separation of the aqueous phase, from the aqueous/organic two-phase mixture which is obtained on conclusion of the treatment protocol of the reaction mixture of the process in accordance with the present invention taken from its second subject; this procedure (still more preferred) is particularly advantageous because it makes it possible to link together the condensation reaction (second subject of the invention) and the hydrolysis reaction (third subject of the invention) while working in the same equipment, without it being necessary to isolate the β-aminovinyl ketone on conclusion of the condensation reaction and without it being necessary to fundamentally change the composition of the reaction mixture in order to pass from the condensation reaction to the hydrolysis reaction.

The hydrolysis reaction is carried out at a temperature lying in the range from 40° C. to 120° C.; when the hydrolysis reaction is carried out in solvent medium, the temperature chosen is then preferably that, in the above-mentioned range, which corresponds to the reflux temperature of the reaction mixture.

The duration of the reaction can vary, depending on the temperature chosen, between, for example, 30 minutes and 5 hours.

The reaction is preferably carried out with the following proportions of ingredients:
β-aminovinyl ketone of formula (VI): 1 mol,
Water: 1 to 20 mol and preferably 1.5–10 mol
Strong acid: 1 to 6 $H^+$ ions and preferably 1.1 to 4 $H^+$ ions.

Strong, inorganic or organic, acid is understood to mean in particular an optionally oxygen-containing mono- or polyacid, at least one of the acid functional groups of which (when there are a number of them) has an ionization constant in water, pKa, which is less than or equal to 3. Mention may be made, as acids of this type, of, from inorganic acids, hydrochloric, sulphuric, orthophosphoric and pyrophosphoric acids. Mention may be made, among organic acids, of: organosulphonic acids, in particular para-toluenesulphonic, methanesulphonic and naphthalenesulphonic acids; organophosphonic acids, in particular monoalkyl- or monoarylphosphonic acids such as methylphosphonic or benzenephosphonic acid; or strong halogenated polycarboxylic acids such as dihalo- and trihalo- (especially chloro and fluoro) acetic or propionic acids. In the invention, it is preferable to use, as strong acid, optionally oxygen-containing inorganic mono- or polyacids and more particularly hydrochloric and sulphuric acids.

The water and the strong acid, which are necessary for the reaction, can advantageously be introduced together into the mixture in the form of an aqueous acidic solution, the normality and the amount of which are determined so as to contribute the required amount of water and the required number of $H^+$ ions.

When all the β-aminovinyl ketone has reacted, the reaction is brought to an end by cooling the reaction mixture and by then treating this mixture, in a way known per se, in order to isolate the β-diketone formed of formula (XI) therefrom.

For example, when the hydrolysis reaction is carried out in a water-immiscible solvent medium, an aqueous/organic two-phase reaction mixture is then present and this treatment can then consist in separating the organic phase which contains the β-diketone formed, for example by settling, and in then concentrating the said organic phase by removal of the reaction solvent(s).

When the hydrolysis reaction is carried out by starting from a mixture based on aminovinyl ketone, the pyrimidine and/or amide (which has not been substantially modified in the hydrolysis reaction) by-product(s), which have been spoken about above, are generally found in the final organic phase, in addition to the β-diketone.

After removal of the solvent(s), the β-diketone obtained can be purified, if necessary, by recrystallization in a way known per se.

The following examples, given without implied limitation, illustrate the invention and show how it can be put into practice.

EXAMPLE 1

Example of the preparation of a β-aminovinyl ketone according to the process of the invention taken from its second subject.

The equipment used consists of a 100-ml, 3-necked, round-bottomed, glass flask equipped with a thermometer, a vertically-mounted reflux condenser, a heating system, a stirring system and a system for passing argon under a slight positive pressure.

The following are successively added to the reactor at room temperature (25° C.):
10.9 g (0.050 mol) of 1-cyano-2-methylthio-4-trifluoromethylbenzene
50 cm³ of methyl tert-butyl ether
7.5 cm³ (0.075 mol) of cyclopropyl methyl ketone, and
7.2 g (0.075 mol) of sodium tert-butoxide in the pure state.

This mixture is stirred and heated at reflux (37° C.) for 3 hours 30 minutes.

After cooling to room temperature, 25 cm³ of a 1N aqueous HCl solution is added to the reaction mixture which brings the pH to a neutral value and results in the production of an aqueous/organic two-phase mixture.

The aqueous phase and the organic phase are separated. The organic phase is then extracted with 25 cm³ of water and it is then concentrated by removal of the solvent by distillation under reduced pressure.

The residual product thus obtained is analysed by high performance liquid chromatography. The results of this analysis are the following:
1) molar degree of conversion of the starting nitrile: 100%,
2) a mixture of the 3 following compounds is formed:

2.1. β-Aminovinyl ketone of formula:

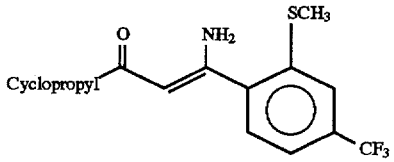

with a molar yield, with respect to the reacted nitrile, equal to 92%;

2.2. Pyrimidine of formula:

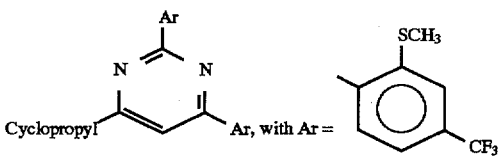

with a molar yield, with respect to the reacted nitrile, equal to 4%; and 2.3. Amide of formula:

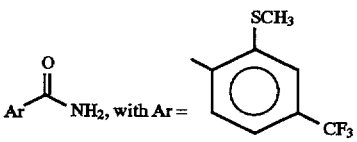

with a molar yield, with respect to the reacted nitrile, equal to 4%.

The β-aminovinyl ketone in the pure state was obtained by recrystallization of the abovementioned mixture from 50 cm³ of toluene. NMR and IR analyses and the mass spectrum are in agreement with the structure presented above:
NMR ($^1$H, CDCl$_3$): 0.75–0.98 ppm (m, 4H), 1.71 ppm (m, 1H), 2.44 ppm (s, 3H), 5.0 ppm (s, 1H), 5.28 ppm (s, 1H), 7.38 ppm (m, 3H), 9.65 ppm (s, 1H);
IR spectrum: 3413–3254 cm$^{-1}$ (NH$_2$), 1613 cm$^{-1}$ (C=O), 1320–1140 cm$^{-1}$ (CF$_3$), 2924 cm$^{-1}$ (SCH$_3$);
mass spectrum (apparatus: VG ZAB 2 S F; source: EICI; M/ΔM=2000): M=301 g.

EXAMPLE 2

Example of the preparation of a β-diketone according to a condition of use in accordance with the invention taken from its third subject.

The equipment used is that already described in Example 1.

Example 1 is reproduced exactly as shown but is halted at the stage of obtaining the aqueous/organic two-phase mixture and the aqueous phase is separated from the organic phase which is left in the reactor used. This organic phase contains the three compounds 2.1., 2.2. and 2.3. which have been described above in Example 1.

10 cm³ of a 10N aqueous sulphuric acid solution are then added to the organic phase. A new aqueous/organic two-phase mixture is formed in this way, which is stirred and heated at 60° C. for 3 hours.

At the end of this time, after cooling to room temperature (25° C.), the two phases are separated. The organic phase is extracted with 20 cm³ of an aqueous NaHCO$_3$ solution containing 5 g of bicarbonate per liter and then with 20 cm³ of water. The solvent of the organic phase is then removed. The residual product obtained is recrystallized from 40 cm³ of methanol and it results, in this way, in the production of the β-diketone, in the pure state, of formula:

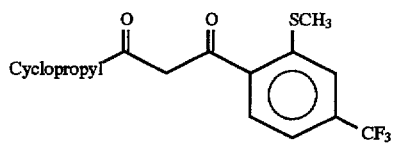

The NMR and mass spectrometric analyses are in agreement with the structure shown above:
NMR ($^1$H, CDCl$_3$):
enol form (90 mol %): 0.96–1.17 ppm (mn 4H), 1.09 ppm (m, 1H), 2.45 ppm (s, 3H), 6.03 ppm (s, 1H for =CH—CO), 7.35–7.56 ppm (m, 3H), >11 ppm (s, 1H);
ketone form (10 mol %): 4.2 ppm (s, 2H for CO—CH$_2$—CO);
mass spectrum: M=302 g;
to be further noted: M.p.=60° C.

We claim:
1. β-Aminovinyl ketones of general formula:

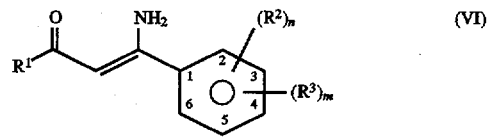

in which:
R$^1$ represents:
a straight- or branched-chain alkenyl or alkynyl group containing up to 6 carbon atoms which is optionally substituted with one or a number of halogen atom(s) and whose unsaturation is not conjugated with the ketone double bond;

a cycloalkyl group containing 3 to 6 carbon atoms, optionally substituted with one or a number of R$^4$ or OR$^4$ group(s) or one or a number of halogen atom(s);

a cycloalkenyl group containing 4 to 6 carbon atoms, optionally substituted with one or a number of R$^4$ or OR$^4$ group(s) or one or a number of halogen atom(s), in which the ethylenic unsaturation is not conjugated with the ketone double bond;

a group of formula (R$^5$)$_p$-phenyl-(CR$^6$R$^7$)$_q$—;

R$^4$ being a straight- or branched-chain alkyl group containing up to 4 carbon atoms;

R$^5$ being a straight- or branched-chain alkyl group containing up to 4 carbon atoms or a halogen atom (F, Cl, Br or I);

R$^6$ and R$^7$, which can be identical or different, each representing a straight- or branched-chain alkyl group containing up to 4 carbon atoms;

p and q being integers, which can be identical or different, ranging from 0 to 3;

R$^2$ represents an electron-withdrawing substituent chosen from the group formed by:
a nitro group;
a COR$^4$ acyl group;
a COOR$^8$ group;

an SR⁴ alkylthio group;

a CONR⁸R⁹ carbamoyl or CSNR⁸R⁹ thiocarbamoyl group;

a linear or branched haloalkyl or haloalkoxy group having up to 4 carbon atoms and in which the halo substitution is a monosubstitution which can range up to a virtually complete polysubstitution;

R⁴ having the general definitions shown above;

R⁸ and R⁹, which can be identical or different, each representing a hydrogen atom or a straight- or branched-chain alkyl group containing up to 4 carbon atoms;

R³ represents:

a straight- or branched-chain alkyl or alkoxy group containing up to 4 carbon atoms, it being possible for the alkyl group to be optionally substituted with an OR⁴ group;

a halogen atom;

a group of formula O—(CH₂)ᵣ—OR⁴;

R⁴ possessing the general definition shown above and r being an integer ranging from 1 to 4;

the n symbol represents an integer ranging from 0 to 2 and the m symbol represents an integer ranging from 0 to 3;

with the following provisos a) and b):

a) R⁵ is other than a chlorine atom when R³ is a chlorine atom and q=0, b) when n, m and q are all equal to zero, then p is other than zero.

2. β-Aminovinyl ketones according to claim 1, characterized in that they correspond to the formula (VI) in which the n symbol represents a number ranging from 1 to 2 and the m symbol represents a number ranging from 0 to 3.

3. β-Aminovinyl ketones according to claim 2, characterized in that these are compounds in the structure of which:

R¹ represents a cycloalkyl group containing 3 to 6 carbon atoms, optionally substituted with one or a number of R⁴ or OR⁴ group(s);

R² represents an SR⁴ alkylthio group or a linear or branched haloalkyl or haloalkoxy group having up to 4 carbon atoms and in which the halo substitution is a monosubstitution which can range up to a virtually complete polysubstitution;

R³ represents a straight- or branched-chain alkyl or alkoxy group containing up to 4 carbon atoms or a halogen atom.

4. β-Aminovinyl ketones according to claim 3, characterized in that these are compounds in the structure of which: the n symbol represents an integer equal to 1 or 2 and the m symbol represents an integer ranging from 0 to 2, with the additional condition according to which the sum of m+n is not more than 3;

the group or one of the groups represented by (R²)ₙ is in the 2-position on the phenyl ring whereas the optional other group(s) represented by (R²)ₙ and/or (R³)ₘ are in the 3- and/or 4-position on the phenyl ring.

5. β-Aminovinyl ketones according to claim 4, characterized in that these are compounds in the structure of which:

R¹ represents a cyclopropyl or 1-methylcyclopropyl group;

R² represents a methylthio or ethylthio group or a trifluoromethyl or trifluoromethoxy group;

R³ represents a methyl, ethyl, methoxy or ethoxy group or a chlorine, bromine or fluorine atom.

6. Process for the preparation of the β-aminovinyl ketones of formula (VI) according to any one of claims 1 to 5, characterized in that it comprises the condensation reaction of a methyl organo ketone of formula:

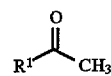

(VII)

in which R¹ has one of the general or preferred definitions shown above with respect to the formula (VI), with an aromatic nitrile of formula:

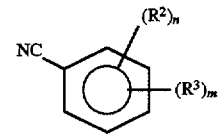

(VIII)

in which the R², R³, n and m symbols have one of the general or preferred definitions shown above with respect to the formula (VI), the said condensation reaction being carried out under an inert atmosphere, with prolonged heating, in inert solvent medium, in the presence of a strong base taken from the group formed by:

(i) alkoxides derived from alkali metals and primary monoalcohols in the structure of which the residue associated with the CH₂OH group is a branched-chain group in which the carbon atom directly bonded to the CH₂OH group is itself bonded to 2 or 3 other carbon atoms, these other carbon atoms belonging to identical or different radicals each chosen from a linear or branched alkyl radical having up to 3 carbon atoms and a phenyl radical;

(2i) alkoxides derived from alkali metals and secondary or tertiary monoalcohols in the structure of which each of the 2 identical or different residues associated with the CHOH group, in the case of secondary alcohols, or each of the 3 identical or different residues associated with the CON group, in the case of tertiary alcohols, consists of a radical chosen from a linear or branched alkyl radical having up to 4 carbon atoms and a phenyl radical; and (3i) solutions of the (i) or (2i) alkoxides in the monoalcohols in which they have been prepared, and in that it optionally produces mixtures based on aminovinyl ketones comprising, in addition to the compound VI, in particular a pyrimidine of general formula:

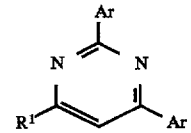

(IX)

in which the Ar symbols, which are identical to each other and represent the group:

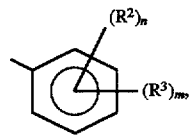

and the R¹ symbol have the general or preferred definitions shown above with respect to the aminovinyl ketone of formula (VI) in any one of claims 1 to 5, with the following provisos for this compound IX:

(a) when n: 0 and m=0 or (b) when n=0 and m=1 or 2 and R³ represents an alkyl or alkoxy group or a halogen atom, R¹ in each case (a) or (b) is then other than an alkyl group or than a group of formula (R⁵-)ₚ-phenyl-(-CR⁶R⁷)q- where q=0;

(c) when n=1 and m=0 and R² represents NO₂, R¹ is then other than a group of formula (R⁵-)ₚ-phenyl-(-CR⁶R⁷)q- where q=0.

7. Process according to claim 6, characterized in that the solvent medium consists of an inert solvent or a mixture of inert solvents chosen from water-immiscible aprotic polar solvents.

8. Process according to claim 6, characterized in that the reaction is carried out with the following molar proportions of ingredients:
aromatic nitrile of formula (VIII): 1 mol
$R^1$ methyl ketone of formula (VII): 1 to 4 mol
alkoxide: 1 to 4 mol.

9. Process according to claim 6, characterized in that the condensation reaction is carried out in the presence of a strong base taken from the group formed by:
(4i) alkoxides derived from alkali metals and tertiary monoalcohols in the structure of which each of the 3 identical or different residues associated with the COH group is a radical chosen from a linear alkyl radical having 1 or 2 carbon atoms and a phenyl radical; and
(5i) solutions of the (4i) alkoxides in the monoalcohols in which they have been prepared.

10. Process according to claim 9, characterized in that the targeted alkoxides are the sodium and potassium alkoxides derived from the following alcohols of formula: $(CH_3)_3$—COH, $(CH_3)_2(C_6H_5)$—COH and $(C_6H_5)_3$—COH.

11. Process according to claim 6, characterized in that the reaction is carried out at a temperature lying in the range from 30° C. to 120° C.

12. A process for the preparation of a β-diketone having the formula

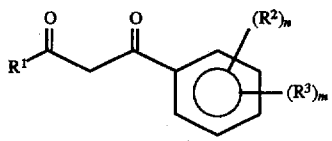

(XI)

wherein $R^1$, $R^2$, $R^3$, n and m are as defined in claim 1, comprising subjecting to hydrolysis the corresponding β-aminovinyl ketone having formula (VI) as defined in claim 1 or subjecting a mixture of said β-aminovinyl ketone having formula (VI) with a minor amount of at least one compound selected from the group consisting of a pyrimidine having the formula

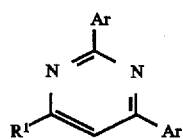

(IX)

and an amide having the formula

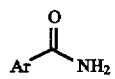

(X)

wherein the Ar groups are identical to one another and have the formula

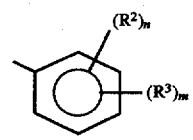

and $R^1$, $R^2$, $R^3$, n and m are defined as above, said hydrolysis being carried out, optionally in an inert solvent medium, in the presence of water and a strong inorganic or organic acid.

13. A process for the preparation of a β-diketone having the formula

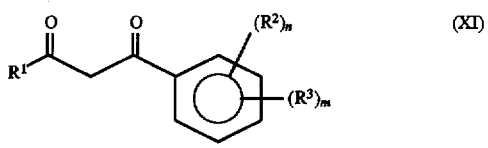

(XI)

wherein $R^1$, $R^2$, $R^3$, n and m are as defined in claim 6, comprising subjecting to hydrolysis the corresponding β-aminovinyl ketone having formula (VI) as defined in claim 1 or subjecting a mixture of said β-aminovinyl ketone having formula (VI) with a minor amount of at least one compound selected from the group consisting of a pyrimidine having the formula

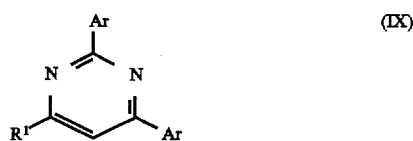

(IX)

and an amide having the formula

(X)

wherein the Ar groups are identical to one another and have the formula

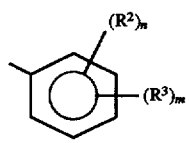

and $R^1$, $R^2$, $R^3$, n and m are defined as above, said hydrolysis being carried out, optionally in an inert solvent medium, in the presence of water and a strong inorganic or organic acid, said inert solvent medium being identical to the inert solvent medium in which the β-aminovinyl ketone starting material having formula (VI) is prepared, said inert solvent medium being as defined in claim 6.

14. A process according to claim 13, wherein said inert solvent medium consists of one or more water-immiscible aprotic polar solvents.

15. A process according to claim 12, wherein 1 mol of β-aminovinyl ketone having formula (VI) is hydrolyzed in the presence of 1 to 20 mol of water and 1 to 6 $H^+$ ions of a strong inorganic or organic acid.

16. A process according to claim 12, wherein the strong inorganic or organic acid has an ionization constant in water, pKa, which is less than or equal to 3.

17. A process according to claim 16, wherein said acid is selected from the group consisting of inorganic acids, organosulphonic acids, organophosphonic acids and halogenated carboxylic acids.

18. A process according to claim 12, wherein said hydrolysis is carried out at a temperature of from 40° C. to 120° C.

* * * * *